United States Patent [19]
Northmore et al.

[11] 3,955,924
[45] May 11, 1976

[54] METHOD FOR THE DETERMINATION OF TOTAL CARBON IN AQUEOUS SOLUTIONS

[75] Inventors: Barry Robert Northmore, Epsom; Kevin John Saunders, Tadworth; Derek Chester White, New Malden, all of England

[73] Assignee: The British Petroleum Company Limited, London, England

[22] Filed: Mar. 19, 1975

[21] Appl. No.: 559,929

[30] Foreign Application Priority Data
Mar. 22, 1974 United Kingdom............... 12792/74

[52] U.S. Cl.......................... 23/230 PC; 23/253 PC
[51] Int. Cl.² ................. G01N 31/08; G01N 31/12; G01N 33/18
[58] Field of Search................... 23/230 PC, 253 PC

[56] References Cited
UNITED STATES PATENTS
3,762,878 10/1973 Villalobos......................... 23/232 E FOREIGN PATENTS OR APPLICATIONS
1,174,261 12/1969 United Kingdom

*Primary Examiner*—Robert M. Reese
*Attorney, Agent, or Firm*—Brooks Haidt Haffner & Delahunty

[57] ABSTRACT

A method for the determination of total carbon, calculated as carbon dioxide, present in aqueous solutions containing organic compounds and/or inorganic carbonates by mixing the aqueous solution with a solid reagent active at elevated temperature for the displacement of carbon dioxide from inorganic carbonates, contacting the mixture with oxygen at elevated temperature whereby carbon dioxide is produced by oxidation of organic compounds and by displacement from any inorganic carbonates present, drying the carbon dioxide so produced, separating the carbon dioxide from the oxygen by selective adsorption on a bed of particulate adsorbent which preferentially retards the passage of carbon dioxide, flushing the bed with inert gas to displace the oxygen, thereafter eluting the carbon dioxide by raising the temperature and reversing the flow of inert gas through the bed and finally measuring the eluted carbon dioxide.

20 Claims, 4 Drawing Figures

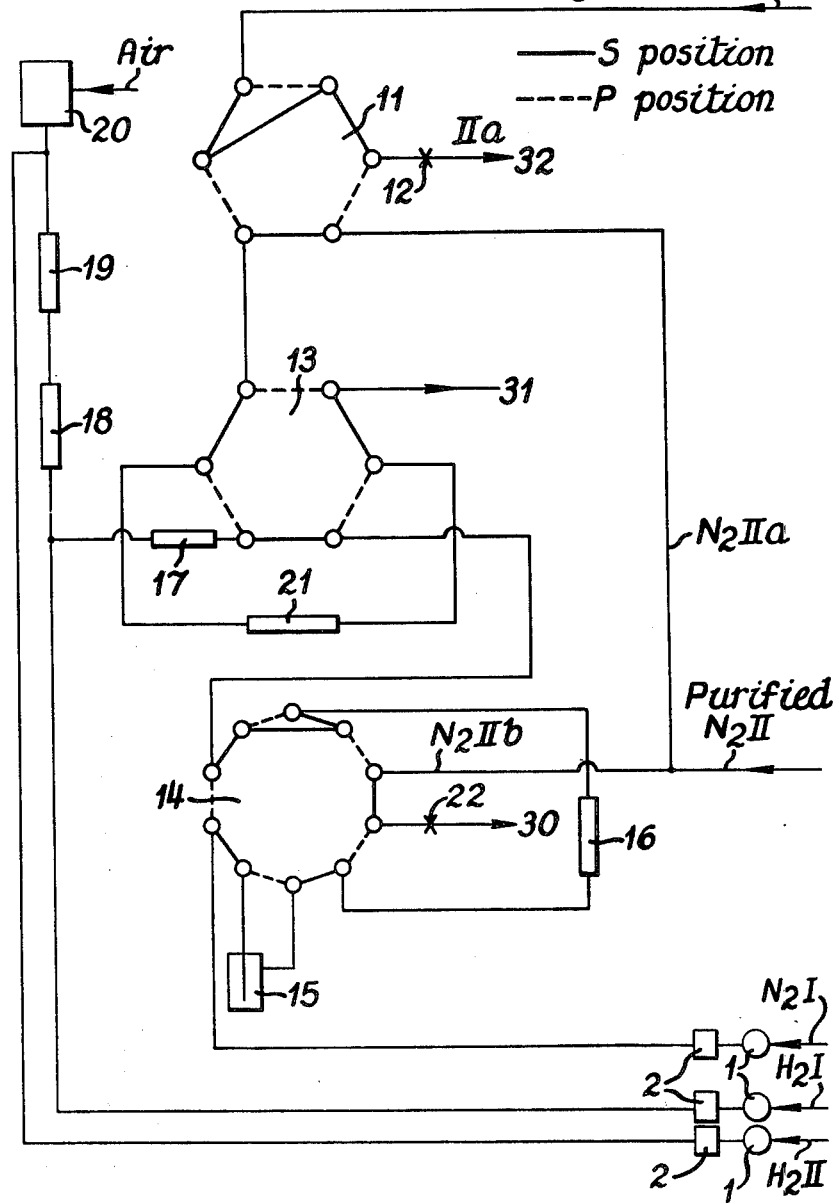

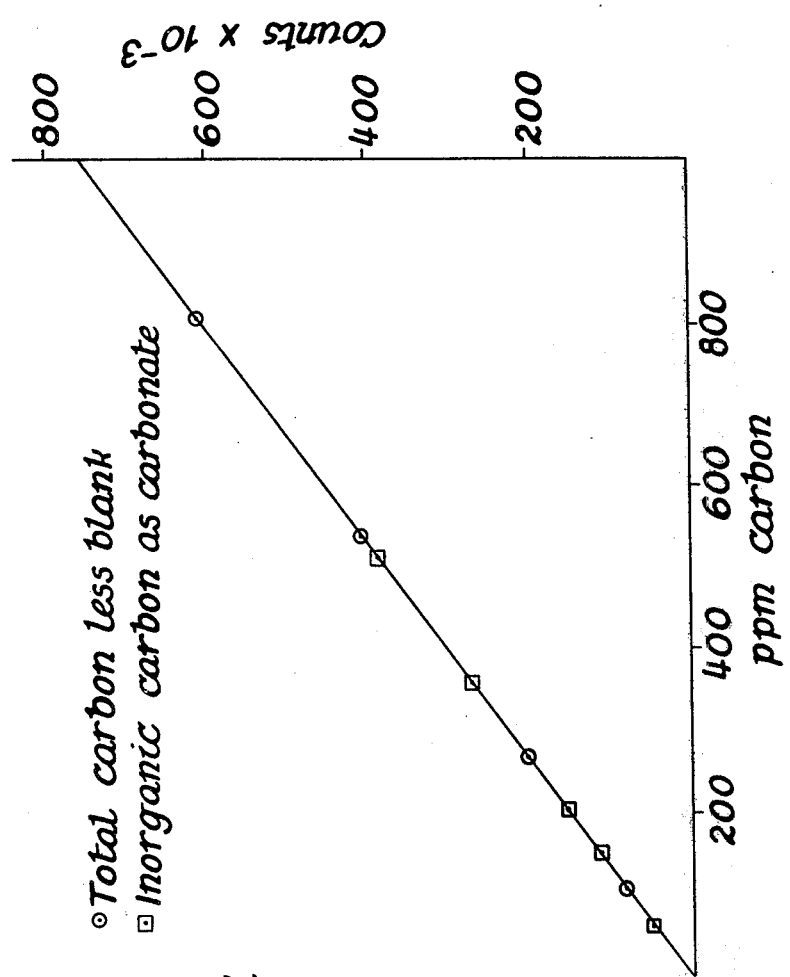

METHOD FOR THE DETERMINATION OF TOTAL CARBON IN AQUEOUS SOLUTIONS

The present invention relates to an improved method for the determination of total carbon in the form of organic compounds and inorganic carbonates in aqueous solutions, optionally containing other inorgainc salts, and to an apparatus suitable for carrying out the method.

The determination of total carbon in aqueous solution is an analytical exercise commonly encountered in industry. For example it is often necessary to carefully monitor the carbon content of recycle streams in chemical processes and in effluents discharged to waste. British Patent Specification No. 1,174,261 describes and claims a method for the determination of total organic matter in aqueous liquors, the method comprising in combination the steps of (1) oxidising a sample of the liquor by bringing it into contact with a solid oxidising agent which is insoluble in the liquor, (2) reducing the carbon dioxide so formed to methane by admixing it with hydrogen and bringing the mixture into contact with a suitable catalyst, (3) quantitatively measuring the methane formed by means of a flame ionisation detector. An apparatus in which the method may be performed comprises an oxidation unit provided with an injection port for a sample of the aqueous liquor and an inlet for an inert carrier gas and incorporating a solid oxidising agent insoluble in the aqueous liquor in contact with which the organic matter in the liquor is oxidised to carbon dioxide, an exit passage from the oxidation unit having an inlet for hydrogen and leading to a reduction unit which incorporates a suitable catalyst whereby the carbon dioxide is reduced in the presence of the hydrogen to methane, and an exit passage from the reduction unit leading to a flame ionisation detector whereby the methane formed is measured. In a preferred embodiment a known volume of sample is dropped onto a bed of copper oxide as oxidising agent at 900°C producing carbon dioxide which is reduced to methane and estimated by flame ionisation. The measurement of organic carbon in aqueous media using this technique tends to be unreliable, particularly when the aqueous media contains non volatile materials, polymers, compounds having a high molecular weight and boiling point or a high concentration of inorganic material. The reason for this is probably repeated deposition of involatile materials on the top of the copper oxide bed, thus reducing its oxidation efficiency. Further problems are encountered in the injection of an aqueous solution, through a rubber septum, whereby fragments of the septum are carried into a furnace 900°C. also the samples tend to spit and splash on to the walls leading to incomplete oxidation.

The above and other disadvantages are substantially overcome by the method and apparatus of the present invention.

Thus according to the present invention there is provided a method for the determination of total carbon present in aqueous solutions containing organic compounds and/or inorganic carbonates, optionally in the presence of other inorganic salts which comprises mixing the aqueous solution at ambient temperature with a solid reagent active at elevated temperature for the displacement of carbon dioxide from inorganic carbonates, contacting the mixture with oxygen at elevated temperature whereby carbon dioxide is produced by oxidation of organic compounds and by displacement from any inorganic carbonates present, drying the carbon dioxide so-produced, collecting at least all the carbon dioxide in the gaseous mixture by passing the mixture at low temperature through a column packed with a sorbent phase which selectively retards the passage of carbon dioxide, displacing the oxygen from the sorbent phase by passing an inert gas therethrough, thereafter eluting carbon dioxide by raising the temperature and passing inert gas in the reverse direction and finally quantitatively measuring the eluted carbon dioxide.

The carbon dioxide may be directly measured by an infra-red analyser or, indirectly by converting it to methane by contact with hydrogen in the presence of a catalyst active for the chemical reduction thereof and subsequently quantitatively measuring the methane so-formed by a flame ionisaton detector.

The reduction catalyst is preferably nickel supported on fire-brick maintainend at a temperature of above 275°C, preferably a temperature in the range 300° to 500°, even more preferably 350° to 400°C. The catalyst may suitably be prepared by slurrying the fire-brick with a saturated aqueous solution of a nickel nitrate, removing the excess aqueous solution, drying, heating to a temperature sufficient to produce nickel oxide and finally reducing the nickel oxide to nickel in a stream of hydrogen/inert gas at elevated temperature e.g. 250°C. For the purpose of bringing about the reduction of carbon dioxide, a suitable proportion of hydrogen is admixed with the inert gas and carbon dioxide feed to the reduction catalyst.

The choice of solid reagent active for the displacement of carbon dioxide from inorganic carbonates depends on the composition of the aqueous solution under examination. In the absence of free halogen in the aqueous solution suitable reagents are, for example vanadium pentoxide, tungstic oxide, silver orthovanadate or magnesium oxide/silver oxide/silver tungstate. The reagents are preferably mixed with an inert adsorbent, for example asbestos, pumice, fire-brick etc. The preferred reagent is vanadium pentoxide mixed with pumice, suitably in the proportion of 1 part by weight vanadium pentoxide to 4 parts by weight pumice. In the presence of free halogen in the aqueous solution suitable reagents are silver orthovanadate and magnesium oxide/silver oxide/silver tungstate, preferably mixed with an inert adsorbent such as asbestos, pumice fire-brick etc. The preferred reagent in the presence of free halogen is a silver orthovanadate/pumice mixture in a weight ratio of 1:4. Organic carbon compounds are oxidised at elevated temperature in the stream of oxygen which also serves as a carrier for the carbon dioxide formed. It is preferably to purify the oxygen. This may suitably be achieved by passage through a silica tube packed with platinised asbestos maintained at 600° to 1000°C. The carbon dioxide and water formed by oxidation of any carbon compound impurities in the oxygen may be removed by passing the gas stream through a vessel charged with soda asbestos and magnesium perchlorate.

The carbon dioxide in the gaseous mixture is collected by passing the mixture at low temperature through a column packed with a sorbent phase which selectively retards the passage of carbon dioxide followed by displacing oxygen from the sorbent phase with a stream of inert gas. Whilst the sorbent phase may be any material which retards the passage of carbon dioxide to a greater degree than the passage of oxygen and inert gas suitable materials are molecular sieves and crosslinked polymeric materials. A particularly suitable sorbent phase is a crosslinked polystyrene material manufactured and sold by the Dow Chemical Co. Ltd., under the trade name "Porapak Q" (Registered Trade Mark). The sorbent phase is suitably maintained at a temperature in the range −65° to −90°C, preferably at a temperature of about −78°C, during the passage of the mixture of carbon dioxide and oxygen. A temperature of −78°C may suitably be achieved using a mixture of acetone and solid carbon dioxide. By passing a stream of inert gas through the sorbent phase oxygen is displaced and replaced by inert gas. In order to elute the carbon dioxide from the sorbent phase the passage of an inert gas is continued, in the reverse direction whilst raising the temperature to, for example, room temperature. The carbon dioxide and inert gas may be quantitatively transferred either to an infra-red analyser or is combined with hydrogen and passes over a reduction catalyst. After contacting the reduction catalyst the gas stream consisting of inert gas, hydrogen, methane and water, may be passed directly to a flame ionisation detector. On the other hand it is preferred to dry the gas stream prior to entering the detector because the detector's response may be affected by the presence of water. The gas stream may be drid by contact with, for example, self-indicating silica gel.

In order that the recorded signal from the flame ionisation detector or the infra-red analyser may be interpreted directly in terms of total carbon content of the samples submitted to test, it is necessary to calibrate the detector or analyser equipment with standard aqueous solutions containing organic carbon and/or inorganic carbonate.

In order to obtain the amount of organic carbon as distinct from total carbon present in an aqueous sample, should it be desired, it is necessary to make an additional measurement of the contribution of the inorganic carbon present in the aqueous sample to the total carbon measurement. If the aqueous solution containing the organic compounds and/or inorganic carbonates is free from volatile organic compounds such as low-boiling alcohols, chlorides, esters, carbonyls, ethers, aromatic and aliphatic hydrocarbons, measurement of the contribution of the inorganic carbonate to the total carbon content may be accomplished simply by reacting a separate sample of the same aqueous solution with a mineral acid e.g. dilute sulphuric acid, or a mixture of mineral acid and hydrogen peroxide if the sample contains chlorine, removing the carbon dioxide liberated in a stream of inert gas and thereafter measuring the amount of carbon dioxide evolved by an infra-red analyser or converting to methane by chemical reduction in the presence of a catalyst and hydrogen and measuring the amount of methane in a flame ionisation detector as hereinbefore described.

However, if the aqueous solution contains volatile organic compounds such as those hereinbefore described their presence may interfere with the measurement of inorganic carbonate if the evolved carbon dioxide is measured by reduction followed by measurement of the resulting methane in a flame ionisation detector. Measurement of the evolved carbon dioxide by infra-red analysis is not affected by volatile organic compounds and this method may be used in the presence of such compounds.

It is preferred to measure the contribution of the inorganic carbonate to the total carbon content of aqueous solutions containing organic compounds and/or inorganic carbonates optionally in the presence of other inorganic compounds by reacting a separate sample of the same aqueous solution with a mineral acid, or a mixture of mineral acid and hydrogen peroxide if the sample contains chlorine, removing the liberated carbon dioxide in a stream of inert gas, passing the gaseous mixture of carbon dioxide and inert gas through a column packed with a sorbent phase which preferentially retards the passage of organic compounds, whilst allowing the passage of carbon dioxide and thereafter quantitatively measuring the carbon dioxide by chemical reduction to methane in the presence of a catalyst and hydrogen and measuring the resulting methane in a flame ionisation detector.

Whilst the sorbent phase may be any material which retards the passage of organic compounds to a greater degree than the passage of carbon dioxide and inert gas suitable materials are molecular sieves and crosslinked polymeric materials. A particularly preferred material is a crosslinked polystyrene manufactured and sold by the Dow Chemical Co. Ltd. under the Registered Trade Mark "Porapak Q". The passage of the gaseous mixture of carbon dioxide and inert gas through the column packed with a sorbent phase is suitably effected at ambient temperature.

The determination of total inorganic carbonate is preferably carried out whilst the carbon dioxide resulting from the total carbon determination is being separated from oxygen by passage through the column of sorbent phase maintained at low temperature, the inert gas stream used to remove the carbon dioxide liberated from the inorganic carbonate then being used to elute the carbon dioxide from the column.

Between each measurement of the inorganic carbonate contribution to the total carbon content it is preferred to remove organic compounds from the sorbent phase by passing an inert gas through the column in the reverse direction.

Whilst any inert gas may be used to displace oxygen and elute carbon dioxide from the sorbent phase in the total carbon determination and to remove organic compound from the sorbent phase in the measurement of the contribution of the inorganic carbonate to the total carbon content it is preferred to use nitrogen. It is preferred to purify the inert gas before using it to displace oxygen from the sorbent phase in the total carbon determination and to remove organic compounds from the sorbent phase in the inorganic carbonate measurement. When the inert gas is nitrogen it may be purified by passage through a silica tube packed with copper oxide at a temperature in the range 600° to 1000°C.

In order that the recorded signal from the infra-red analyser or the flame ionisation detector may be interrupted directly in terms of inorganic carbon content of the samples submitted to test it is necessary to calibrate the instruments by reacting standard solutions of inorganic carbonate with mineral acid and measuring the signal recorded by the instrument. By using solutions of different concentration a graph of recorded signal versus inorganic carbon content may be plotted.

The method is particularly suitable for the determination of total carbon at levels of 10–1000 $\mu$g/ml. in aqueous streams and in the presence of inorganic salts.

The present invention also includes apparatus suitable for carrying out the method hereinbefore described.

Thus according to another aspect of the present invention there is provided apparatus for the determination of total carbon present in aqueous solutions as organic compounds and inorganic carbonates, optionally in the presence of other inorganic salts, which comprises an oxidation zone comprising in sequence an input section, a pyrolysis section and a reactor section, both the latter sections being provided with heating means, the input section having an oxygen inlet port, a port for the introduction and recovery of a receptacle for solid reagent active at elevated temperature for the displacement of carbon dioxide from inorganic carbonates, additionally incorporating means for transferring the receptacle to and recovering it from the pyrolysis section and a port for charging sample to the receptacle, the reactor section connecting by means of a passage incorporating water removal means to gas-flow directional switching means so adapted as to separately connect the reactor section through a column suitable for the quantitative removal of carbon dioxide to vent, to connect a source of inert gas through the column to vent and to connect a second source of inert gas through the column to means for measuring carbon dioxide.

In a further modification of the apparatus there is provided means for the determination of total inorganic carbonate comprising a vessel, provided with an inert gas inlet port and a port or ports for charging mineral acid and sample, connecting through a passage via the gas-flow directional switching means to the means for measuring carbon dioxide.

Preferably the passage connecting the vessel to the gas-flow directional switching means incorporates an acid splash trap.

Preferably the vessel connects through a passage with a second gas-flow directional switching means adapted to separately connect the vessel with a column suitable for the quantitative removal of organic compounds and thereafter to means for measuring carbon dioxide.

The gas-flow directional switching means is preferably a multi-port valve.

The input section of the oxidation zone may be a silica or metal tube and the pyrolysis section an extension of this tube provided with heating means. The reactor section may be a further extension of this tube, also provided with heating means.

The port through which sample may be charged to the receptacle may be closed by a stopper or preferably by a septumless injection valve. A preferred form of septumless injection valve is a pneumatically operated valve comprising a pressure chamber provided with two in-line hose connections and a port, a flexible tube linking the in-line hose connections to form a continuous passage through the chamber, the flexible tube being such that it collapses to seal the passage on application of pressure through the port and re-opens the said passage on release of said applied pressure.

Preferably the opposed ends of the in-line hose connections are profiled by chamfering.

The flexible tube linking the in-line hose connections is preferably a silicon rubber tube.

The passage connecting the oxidation zone to the gas-flow directional switching means preferably incorporates a water condenser and a tube suitable for magnesium perchlorate.

The oxygen inlet port of the input section of the oxidation zone is preferably connected to a source of oxygen by means of a passage incorporating oxygen purification means, which may suitable be a silica tube packed with platinised asbestos and provided with heating means. The passage from the oxygen purification means to the oxygen inlet port preferably incorporates a tube for soda asbestos for the removal of carbon dioxide.

The receptacle for solid reagent may be a silica, platinum or porcelain boat.

The means for measuring carbon dioxide may be an infra-red analyser. Alternatively and preferably the column connects through a passage incorporating a tube packed with a reduction catalyst and provided with heating means to a flame ionisation detector, the signal from which is fed to an amplifier and an integrator. Immediately prior to the detector it is preferred to incorporate water removal means, suitably in the form of a tube packed with silica gel.

A further preferred feature of the apparatus is a delay tube, suitably in the form of copper tubing wound in a helix, mounted in the passage to the carbon dioxide measuring means and positioned between the gas-flow directional switching means and the water removal means.

By way of illustration a preferred embodiment of the method and apparatus of the invention will now be described with reference to the accompanying drawings in which:

FIG. 2 is a flow diagram illustrating the interconnections of the valve system.

FIG. 4 is a calibration curve.

Figure 1:
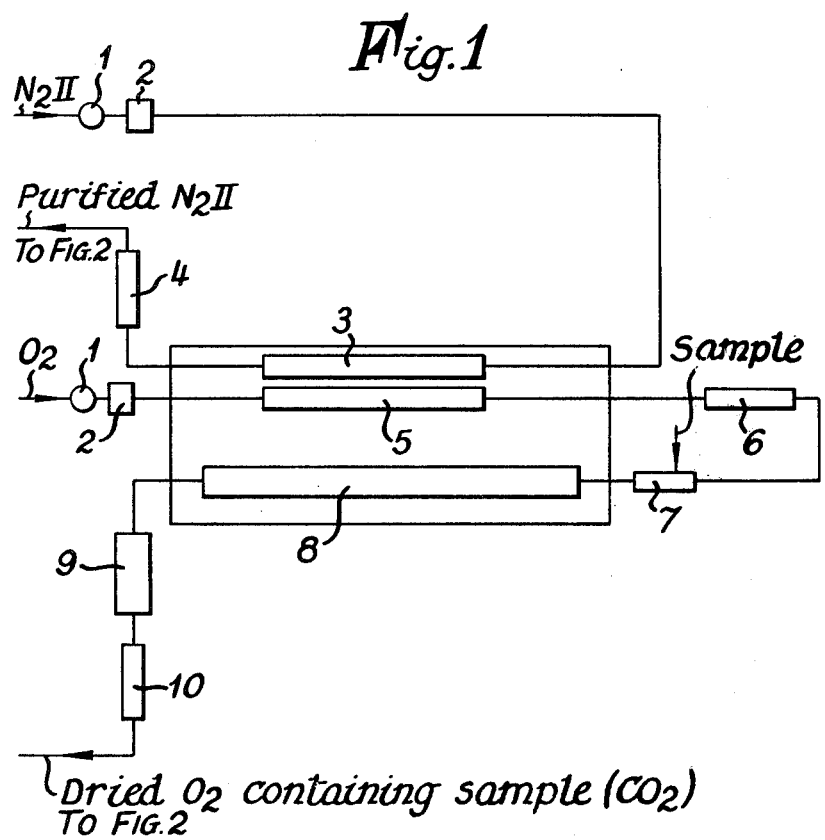
FIG. 1 is a flow diagram of the furnace assembly.

With reference to FIG. 1, 1 are Norgren Miniature Pressure Regulators (Model R06-100-NNEB); 2 are Brooks Constant Mass Flow Controllers; 3 is a silica tube for copper oxide; 4 is a glass trap for soda asbestos; 5 is a silica tube for platinised asbestos; both 3 and 5 are mounted within a furnace (not shown) the temperature of which is controlled by a Robertshaw Skil Ltd. Series 9 Temperature Controller; 6 is a glass tube for soda asbestos; 7 is the input and pyrolysis section of the oxidation zone; 8 is the combustion section of the oxidation zone mounted within a second furnace (not shown) the temperature of which is controlled by a Robertshaw Skil Ltd. Series 9 Temperature Controller; 9 is a water condenser; 10 is a glass tube for magnesium perchlorate.

With reference to FIG. 2, 11 is a pneumatically controlled 6-port SV220 Servomex Slide Valve; 12 is a Drallim Miniature Valve 1500/2; 13 is a pneumatically controlled 6-port SV 220 Servomex Slide Valve; 14 is a pneumatically controlled 10-port SV 234 Servomex Slide Valve; 15 is a carbonate bubbler consisting of a small tube, with a total volume of about 4 ml for 9N sulphuric acid incorporating an acid splash trap containing silica wool (not shown); 16 is the organic volatiles trap consisting of a coil (50 mm diameter) of ¼ in (6 mm) O.D. glass tube, total length 400 mm and tightly wound; 17 is a delay tube consisting of 180 cm. length of 3.2 mm O.D. copper tubing wound in a helix; 18 is the reduction tube which consists of a stainless steel tube wound with 1.0 m of Thermocoax (13.7 ohm/meter) connected to the 12v supply on the Radio Spares Transformer used also as the power supply for the pyrolysis section of the oxidation zone. This gives a temperature of 375° ± 25°C inside the reduction tube 18. The tube is packed before use with a nickel/firebrick catalyst; 19 is a Pyrex glass U-tube of length 75 cm and O.D. 10 mm for silica gel; 20 is a standard Pye Flame Ionisation Detector, coupled with a standard Pye Flame Ionisation Amplifier (not shown), the signal from which is fed to an Infotronics CRS 208 Automatic Digital Integrator (not shown). The Integrator functions are controlled by the apparatus' time sequence which has an override facility; 21 is a coil (of 50 mm diameter) of ¼ in. (6 mm) O.D. glass tubing, total length 550 mm; 22 is a Drallium Miniature Valve 1500/2; 30, 31 and 32 are vents.

Parts of the apparatus briefly referred to above are described in further detail with reference to the appropriate Figures below.

Figure 3:
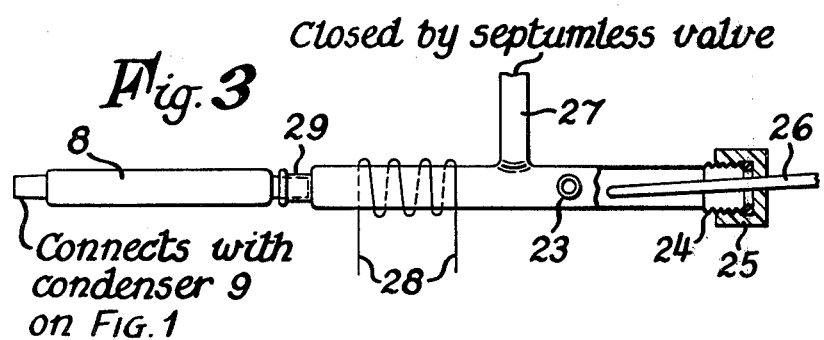
FIG. 3 is a plan-view of the input, pyrolysis and reactor sections forming the oxidation zone.

Thus Figure 3 shows the input, pyrolysis and reactor sections forming the oxidation zone and fabricated from quartz glass. In the Figure 23 is an oxygen entry port; one end of the tube terminates in a threaded silica portion 24 which mates with a plastic cap 25 complete with an O-ring seal, through which cap slides a glass placing rod 26 for moving a porcelain boat (not shown); 27 is an injection port which is closed by the septumless valve described in our copending British Appln. Ser. No. 19266/73 (BP Case No. CIE 3520); 28 is a heating coil consisting of 3m. 19 SWG Bright Ray C resistance wire wrapped around the tube. The power is supplied by a Radio Spares Transformer giving 3 amps at 15 volts, providing sufficient power to maintain a temperature of 200°C, and a Majestic transformer giving 12 amps at 50 volts, providing power for maintaining the temperature at 850° ± 50°C. The tube ends in a B.10 socket 29 which mates with a B.10 cone on one end of the combustion tube 8, the other end of the tube ending in a B.14 cone which mates with a B.14 socket on the condenser 9.

MISCELLANEOUS

The valve 11, 13 and 14 are actuated with Festo Solenoid Valves, Type MC-4-Y8 (240VAC/50Hz). A festo Double Acting Combi Cylinder Type DGS-25-140 is used for raising and lowering a Dewar vessel around the coil 20.

All operations are controlled using a (0–12 min) Varicam Timer. This actuates microswitches which control the sequence of the various functions in the procedure. The timing of these operations follows in the description of the procedure.

A control module (not shown in the Figures) is mounted at the bottom of the reduction tube 18 and detector 20. It contains the timer and associated micro switches, the low temperature alarm and reduction furnace temperature indicator. The manual override functions are mounted on the front panel.

The power to the furnace heaters is fed through a gold strip which melts at 1063°C, thus breaking the circuit and preventing overheating of the furnace.

PREPARATION OF NICKEL/FIREBRICK REDUCTION CATALYST 10 g of 30 to 60 BS mesh firebrick (Chromosorb P) were weighed into 50 ml of a saturated aqueous solution of nickel nitrate and mixed well. The surplus liquor was removed by filtration with gentle suction through a Buchner funnel. The filter-cake was dried overnight at 105°C to 110°C and then heated in a muffle furnace in a fume cupboard for 6 hr. at 400°C to 500°C, at which stage nitrogen oxides are evolved.

The dry material was packed into the reduction tube to give a 10 cm length of packing held in position by silica wool plugs. A hydrogen/nitrogen, 1:1 v/v supply line was attached and a glass exit pipe was attached to the other end. The hydrogen/nitrogen flow was adjusted to 20 ml/min and the effluent gas was burned at the exit pipe. The electrical heater around the reduction tube was switched on and the current adjusted to maintain the temperature at 250° to 260°C. The gas flow was continued for a further 12 hours to effect the reduction of nickel oxide to metallic nickel, in which condition it was ready or use.

PROCEDURE

The procedure developed for using the apparatus is described with reference to the Drawings as follows:

a. Preparation of Apparatus
1. i. 1g of Porapak Q, previously conditioned by heating overnight at a temperature of 180°C in a stream of pure nitrogen flowing at a rate of 50–100 ml/min, was packed into the coil 21 so that it occupied the lower part (250 mm) of the coil.
   ii. 2g Porapak Q, conditioned as in (i) above was placed in the organic volatiles trap 16.
2. The tubes 4 and 6 were filled with soda asbestos.
3. The glass tube 10 was filled with magnesium perchlorate.
4. The tube 19 was filled with self-indicating silica gel (5–20 mesh).
5. The water was turned on to the condenser 9.
6. The gases $N_2I$, $N_2II$, $O_2$, $H_2I$, $H_2II$ and air were switched on and the pressure regulators 1 were set to 30 psi (ca. 2 bars). The flow controllers 2 were adjusted to give the following flows:

| | |
|---|---|
| Oxygen | 80 ml/min |
| $N_2I$ | 60 ml/min |
| $N_2II$ | 300 ml/min |
| $H_2I$ | 60 ml/min |
| $H_2II$ | 10 ml/min |
| Air | 500 ml/min |

(it was necessary to disconnect some lines to measure the flows).

The needle valves 12 and 22 which control the flow of $N_2$ which flushes the Porapak Q coil 21 used to retard carbon dioxide and the $N_2$ which backflushes the Porapak Q organic volatiles trap 16 respectively were adjusted as follows:

The $N_2II$ flow was set to approximately 300 ml/min and valves 11, 13 and 14 were switched to the P-position. With valve 22 fully open valve 12 was adjusted to give approximately 200 ml/min at the vent 30.

Valves 11, 13 and 14 were set to the S-position. Valve 22 was adjusted to give a flow of 90 ml/min at exit vent 31.

Valves 11, 13 and 14 were then reset to the P-position and the flow at exit vent 30 was ascertained to be greater than 120 ml/min.

7. The mains to the control panel, furnaces and transformers was switched on. The power supply to the reduction tube 18 was not affected by the panel switch.
8. After an initial warm-up period the temperatures of the furnaces were checked as follows:
   Reduction tube 18 furnace 350°–400°C Combustion tube 8 furnace 850°–950°C
Purification furnace 750°–850°C 9. The flame on the Flame Ionisation Detector 20 was lit.
10. The amplifier was set up according to the manufacturer's instructions. The integrator was connected via the attenuator box to the integrator connection on the amplifier. The attenuation was set to a value of $1 \times 10^{-8}$ amps FSD giving 4000 counts/ppm carbon.
11. The reset on the control panel was pressed and the reset position of the valves and controls were:
Valves 11, 13 and 14 in the P-position
Furnace heat in the off position
Dewar in the down position
Dewar in the down position
12. The Dewar, for cooling the coil 21, already containing acetone was topped up with solid carbon dioxide.
13. The low level alarm was switched on.
14. With valves 11, 13 and 14 in the P-position 1 ml of 9N sulphuric acid was injected into the carbonate bubbler 15. If the sample under analysis is known to contain free halogen the sulphuric acid in replaced with a mixture of hydrogen peroxide (100 vol) and 2N sulphuric acid (1:1 by volume).
15. With valves 11, 13 and 14 in the P-position the oxygen flow at vent 31 (vent line from valve 13) was determined. The start on the control panel was pressed and the oxygen flow at vent 31 redetermined with valve 11 in the P-position, valves 13 and 14 in the S-position. This operates was performed to check the oxygen flow was the same in both positions of valves 13 and 14. If the flow in the S-position had been slow a leak in the system would have been indicated. Valve 11 was returned to the P-position and valves 13 and 14 to the S-position.
16. A micro porcelain boat (Andermann Type M2a) charged with a mixture of 1 part vanadium pentoxide and 4 parts pumice, pretreated by heating to red-heat in a stream of oxygen for 3 minutes followed by cooling was transferred to the input section 7 of the oxidation zone by removing the plastic cap 25, placing the boat in the tube and replacing cap 25. Using rod 26 the boat was pushed to a point under the injection 27.
17. A Terumo (100 μl) syringe, clean and free from grease was filled with a 100 μl sample for the total carbon determination.
18. The injection valve on the port 27 was opened and the sample was injected into the boat, the boat being in the cold zone of the input section 7.
19. The valve on the injection port 27 was closed.
20. The placing rod 26 was carefully released and the boat was pushed into the zone 28. The start on the control panel was pressed and from then on all operations were controlled by the Varicam Timer which actuates microswitches controlling the sequence of the various operations in the method. From pressing the start there is a delay of 20 seconds followed by valves 13 and 14 switching from the P- to the S-position, the Dewar being raised around the coil 21, the heating zone 28 was then heated to 200°C and the integrator switching to manual and then to automatic operation.
21. The syringe was filled with a 100 μl sample for the inorganic carbonate estimation and immediately injected into the carbonate bubbler 15.
22. At approximately T= 1 m integration of the inorganic carbonate peak began.
23. At T= 2 m the pyrolysis zone 28 was heated to 900°C.
24. At approximately T = 4 m integration of the carbonate peak finished.
25. At T = 5 m heating of the pyrolysis zone 28 was discontinued.
26. At T = 6 m valve 11 switched from the P- to the S-position.
Also the boat replacement buzzer rang indicating that it was time to carefully release the placing rod 26 and use it to remove the boat from the heater zone 28 and then using a pair of tweezers remove it from the injection zone 7. It was immediately replaced with a preconditioned boat as described in step 16.
27. At T = 7½ m the integrator switched to manual.
28. At T = 8 m valves 13 and 14 switched from the S- to the P-position.
Also the Dewar surrounding the coil 21 lowered.
29. At T = 8½ m valve 11 switched from the S- to the P-position.
30. At T = 0 9 m (approx) integration of the total carbon peak began.
31. At T = 12 m (approx) integration of the total carbon peak finished.

When integration was complete the reset on the control panel was pressed.

Although automatic operation of the instrument has been described it is possible, if a failure or malfunction of the timing sequence is encountered or, if desired, to operate the instrument manually at the appropriate sequence times.

CALIBRATION

Preparation of Purified water

Previously distilled water was further purified by distillation from acid dichromate and collected in a flask protected with soda lime. This procedure yielded water containing less than 1 ppm total carbon which was used to prepare all standard solutions.

Preparation of carbonate standards

Sodium carbonate was dried by heating in a platinum crucible at 300°C for 4 hr. About 0.9 g of the dried anhydrous sodium carbonate (11.33% C) accurately weighed, was added to a 100 ml flask and made up to the mark with purified water. Aliquots (50, 20, 15 and 6 ml) of this solution were made up to 100 ml to give solutions containing respectively 510, 204, 153, 61 ppm carbon when exactly 0.900 g sodium carbonate was taken initially.

Preparation of carbon standards

About 1 g of diethylene glycol monoethyl ether (Ethyl Digol) (53.6% C), accurately weighed, was added to a flask (100 ml) and made up to the mark with purified water.

Aliquots (20, 15, 10, 5, 2 ml) of this solution were made up to 100 ml. to give solutions containing 1072, 804, 536, 268 and 107 ppm carbon for 1.00 g Ethyl Digol.

Calibration and calculation procedure

The apparatus was calibrated by injecting the aliquots, as prepared above, in the manner hereinbefore described. It was possible to use the carbonate standards for both total carbon and inorganic carbonate determinations, the ethyl digol being used only for total carbon determination.

The apparatus blank was determined by injecting aliquots (100 µl) of blank water, which was also used to flush the apparatus before the commencement of the analysis determinations.

From a graph of µg/ml carbon against integrator counts, the response per µgC/ml. (i.e. the slope) was calculated. The slopes corresponding to the carbonate standards (total carbon and inorganic carbonate) and ethyl digol (total carbon) should in theory be the same but in practice slight variations (5%) were sometimes found and allowance for this must be made in the calculation. In the total carbon determination the apparatus blank was subtracted from the total carbon value to obtain the true value i.e.

Total carbon = $A/F_t - B$
Total inorganic carbonate = $C/F_{ic}$

Where A = integrator count for total carbon
$F_t$ = response factor (counts per µg C/ml) for total carbon
B = blank for pure water
C = integrator count for inorganic carbonate
$F_{ic}$ = response factor (counts per µg C/ml) for total inorganic carbonate
and organic carbon = total carbon minus inorganic carbonate.

RESULTS

Figures for a typical calibration derived by manual operation of the apparatus are given in the following Tables 1 and 2 and a graph of carbon against integrator counts is given in FIG. 4.

Table 1

| | Carbonate Standards Integrator Counts | | |
|---|---|---|---|
| ppm C | Total Carbon Method | Carbonate Method | Difference |
| 510 | 396 285 | 388 139 | 8146 |
| 357 | 280 039 | 272 859 | 7180 |
| 204 | 168 928 | 158 454 | 10474 |
| 153 | 126 360 | 116 592 | 9768 |
| 61 | 62 135 | 50 921 | 11214 |
| blank | 10 392 | 520 | 9872 | mean difference = 9442
standard deviation of mean difference = 1503
slope of carbonate line = 753

Table 2

| | Ethyl Digol Standards Integrator Counts | |
|---|---|---|
| ppm C | Total Carbon | Total Carbon less Blank |
| 1072 | 820 602 | 810 113 |
| 804 | 620 760 | 610 272 |
| 536 | 420 036 | 409 547 |
| 268 | 215 928 | 205 439 |
| 107 | 94 689 | 84 200 |
| blank | 10 489 | 84 200 |

Slope of Ethyl Digol line = 761

The repeatabilities of the total carbon, carbonate-carbon and the blank are given in the following Table 3.

Table 3

| | Repeatability of Results | | |
|---|---|---|---|
| | ppm C | No. of readings | Standard Deviation |
| Digol | 203 | 12 | 2.86 |
| Blank | 14 | 12 | 2.51 |
| Carbonate | 204 | 12 | 0.94 |

The results of a limited series of precision tests conducted with the automatic embodiment of the apparatus are given in Table 4.

Table 4

| Test Solution (Substance-carbon concentration) | Carbon Determinations-Analytical Precision | | | | | | |
|---|---|---|---|---|---|---|---|
| | Total Carbon Determination | | | | Inorganic Carbon Determination | | |
| | n | Mean Response (counts) | 100S/x | F | n | Mean Response (counts) | 100S/x | F |
| Sucrose-1084µgC/ml | 8 | 450944 | 0.45 | 416 | | | | |
| Butanol-946 µgC/ml | 6 | 392590 | 0.71 | 415 | | | | |
| Ethyl digol 834 µgC/ml | 6 | 336936 | 0.53 | 404 | | | | |
| Sodium carbonate-58µgC/ml | 6 | 24592 | 4.13 | 424 | 6 | 24418 | 0.26 | 421 |
| Sodium carbonate-408 µgC/ml | 6 | 170136 | 1.38 | 417 | 6 | 171768 | 0.27 | 421 |

The carbon blank determined from injections of purified water samples was equivalent to 7 µgC/ml with a relative standard deviation (5 determinations) of 14 percent.

We claim:

1. A method for the determination of total carbon present in aqueous solutions containing organic compounds and/or inorganic carbonates, optionally in the presence of other inorganic salts, which consists of mixing the aqueous solution at ambient temperature with a solid reagent active at elevated temperature for the displacement of carbon dioxide from inorganic carbonates, contacting the mixture with oxygen at elevated temperature whereby carbon dioxide is produced by oxidation of organic compounds and by displacement from any inorganic carbonates present, drying the carbon dioxide so produced, collecting at least all the carbon dioxide in the gaseous mixture by passing the mixture at low temperature through a column packed with a sorbent phase which selectively retards the passage of carbon dioxide, displacing the oxygen from the sorbent phase by passing an inert gas therethrough, thereafter eluting carbon dioxide by raising the temperature and passing inert gas in the reverse direction and finally quantitatively measuring the eluted carbon dioxide.

2. A method according to claim 1 wherein, in the absence of free halogen in the aqueous solution, the solid reagent active at elevated temperature for the displacement of carbon dioxide from inorganic carbonates is selected from vanadium pentoxide, tungstic oxide, silver orthovanadate and magnesium oxide/silver oxide/silver tungstate.

3. A method according to claim 1 wherein, in the presence of free halogen in the aqueous solution, the solid reagent active at elevated temperature for the displacement of carbon dioxide from inorganic carbonates in selected from silver orthovanadate and magnesium oxide/silver oxide/silver tungstate.

4. A method according to claim 1 wherein the solid reagent active at elevated temperature for the displacement of carbon dioxide from inorganic carbonates is mixed with an inert adsorbent selected from asbestos, pumice and firebrick.

5. A method according to claim 1 wherein the oxygen is purified before contact with the reagent by contact with platinised asbestos maintained at a temperature in the range 600° to 1000°C.

6. A method according to claim 1 wherein the sorbent phase is selected from molecular sieves and cross-linked polymeric materials.

7. A method according to claim 1 wherein the amount of carbon dioxide liberated is measured indirectly by converting it to methane by contact with hydrogen in the presence of a reduction catalyst consisting of nickel supported on firebrick maintained at a temperature in the range 300° to 500°C and subsequently measuring the methane so-formed by a flame ionisation detector.

8. A modification of the method claimed in claim 1 wherein the contribution of the inorganic carbonate to the total carbon content of the aqueous solution containing organic compounds is determined by reacting a separate sample of the same aqueous solution with a mineral acid, or a mixture of a mineral acid and hydrogen peroxide if the sample contains chlorine, removing the carbon dioxide liberated in a stream of inert gas and thereafter quantitatively measuring the amount of carbon dioxide liberated.

9. A method according to claim 8 wherein the organic compounds contained in the aqueous solution include volatile organic compounds and the liberated carbon dioxide removed by the stream of inert gas is passed through a column packed with a sorbent phase which preferentially retards the passage of organic compounds whilst allowing the passage of carbon dioxide prior to quantative measurement of the carbon dioxide.

10. A method according to claim 1 wherein the inert gas is nitrogen.

11. A method according to claim 10 wherein the nitrogen is purified by contact with copper oxide at a temperature in the range 600° to 1000°C.

12. Apparatus for the determination of total carbon present is aqueous solutions as organic compounds and/or inorganic carbonates, optionally in the presence of other inorganic salts, which consists of an oxidation zone formed of an input section, a pyrolysis section and a reactor section in series, both the latter sections being provided with heating means, said input section having an oxygen inlet port, a port for the introduction and recovery of a receptacle for solid reagent active at elevated temperature for the displacement of carbon dioxide from inorganic carbonates, additionally incorporating means for transferring the receptacle to and recovering said receptacle from the pyrolysis section and a port for charging sample to the said receptacle, water removal means, gas-flow directional switching means, a column suitable for the quantitative removal of carbon dioxide and means for measuring carbon dioxide wherein said reactor section connects by means of a passage incorporating said water removal means to said gas-flow directional switching means which is so adapted as to separately connect said reactor section through said column suitable for the quantitative removal of carbon dioxide to vent, to connect a source of inert gas through said column to vent and to connect a second source of inert gas through said column via a passage to said means for measuring carbon dioxide.

13. Apparatus according to claim 12 wherein said gas-flow directional switching means is a multi-port valve.

14. Apparatus according to claim 12 wherein said oxygen inlet port of said input section of said oxidation zone is connected to a source of oxygen by means of a passage incorporating oxygen purification means.

15. Apparatus according to claim 12 wherein said port for charging sample to said receptacle is closed by a pneumatically operated valve consisting of a pressure chamber provided with two in-line hose connections and a port, a flexible tube linking the in-line hose connections to form a continuous passage through said chamber, said flexible tube being such that it collapses to seal said passage on application of pressure through said port and reopens and passage on release of said applied pressure.

16. A modification of the apparatus according to claim 12 wherein there is provided means for measuring the contribution of the inorganic carbonate to the total carbon content of the aqueous solution which consists of a vessel provided with inert gas inlet and outlet ports and a port or ports for charging mineral acid and sample, said outlet port connecting through a passage via said gas-flow directional switching means to said means for measuring carbon dioxide.

17. Apparatus according to claim 16 wherein said vessel connects through a passage with a second gas-flow directional switching means adapted to separately connect said vessel with a column adapted for the quantitative removal of organic compounds and thereafter to said means for measuring carbon dioxide.

18. Apparatus according to claim 12 wherein said means for measuring carbon dioxide is a flame ionisation detector when said passage from said gas-flow directional switching means to said means for measuring carbon dioxide incorporates a tube packed with a reduction catalyst and provided with heating means.

19. Apparatus according to claim 18 wherein water removal means is incorporated in said passage immediately prior to said detector.

20. Apparatus according to claim 18 wherein said passage further incorporates a delay tube immediately following said gas-flow directional switching means.

* * * * *

UNITED STATES PATENT AND TRADEMARK OFFICE
CERTIFICATE OF CORRECTION

PATENT NO. : 3,955,924
DATED : May 11, 1976
INVENTOR(S) : BARRY ROBERT NORTHMORE, KEVIN JOHN SAUNDERS and DEREK CHESTER WHITE It is certified that error appears in the above-identified patent and that said Letters Patent are hereby corrected as shown below:

Col. 1, line 54, after "furnace" insert --at--.
same line, "also" should read --Also--.

Col. 2, line 20, correct the spelling of "maintained".
line 54, "preferably" should read --preferred--

Col. 3, line 20, "passes" should read --passed--
line 27, correct the spelling of "dried"

Col. 4, line 59, beginning of line, "rupted" should read --preted--.

Col. 8, line 15, "or" should read --for--

Col. 9, line 16, delete entire line beginning with "Dewar....position", second occurrence.

Col. 13, claim 3, line 26, change "in" to --is--

Col. 14, claim 12, line 5, change "is" to --in--

Signed and Sealed this

Fifth Day of October 1976

[SEAL]

Attest:

RUTH C. MASON
Attesting Officer

C. MARSHALL DANN
Commissioner of Patents and Trademarks